(12) United States Patent
Govil (10) Patent No.: US 10,286,112 B2
(45) Date of Patent: May 14, 2019

(54) BONE MARROW STEM CELL COMPOSITIONS, METHODS OF MAKING, AND USES THEREOF

(71) Applicant: Biologica Technologies, Carlsbad, CA (US)

(72) Inventor: Amit Prakash Govil, Carlsbad, CA (US)

(73) Assignee: ADVANCED BIOLOGICS, LLC, Carlsbad, CA (US)

( * ) Notice: Subject to any disclaimer, the term of this patent is extended or adjusted under 35 U.S.C. 154(b) by 0 days.

(21) Appl. No.: 15/591,678

(22) Filed: May 10, 2017

(65) Prior Publication Data
US 2017/0239392 A1    Aug. 24, 2017

Related U.S. Application Data

(63) Continuation-in-part of application No. 15/525,418, filed as application No. PCT/US2016/056617 on Oct. 12, 2016.

(60) Provisional application No. 62/240,318, filed on Oct. 12, 2015, provisional application No. 62/240,348, filed on Oct. 12, 2015.

(51) Int. Cl.
| | | |
|---|---|---|
| A61L 27/38 | (2006.01) | |
| A61L 27/54 | (2006.01) | |
| A61L 27/36 | (2006.01) | |
| A61K 38/18 | (2006.01) | |
| A61K 38/01 | (2006.01) | |

(52) U.S. Cl.
CPC .......... *A61L 27/3834* (2013.01); *A61K 38/01* (2013.01); *A61K 38/18* (2013.01); *A61L 27/3604* (2013.01); *A61L 27/3608* (2013.01); *A61L 27/3683* (2013.01); *A61L 27/3895* (2013.01); *A61L 27/54* (2013.01); *A61L 2300/414* (2013.01); *A61L 2430/02* (2013.01); *A61L 2430/38* (2013.01)

(58) Field of Classification Search
None
See application file for complete search history.

(56) References Cited

U.S. PATENT DOCUMENTS

2010/0152863 A1    6/2010    Govil

FOREIGN PATENT DOCUMENTS

WO    2014/151019 A2    9/2014

OTHER PUBLICATIONS

International Search Report for PCT/US2016/056617 dated Feb. 21, 2017.

*Primary Examiner* — David W Berke-Schlessel
(74) *Attorney, Agent, or Firm* — Thomas | Horstemeyer, LLP (57) ABSTRACT

Provided herein are bone marrow stem cell compositions and implants and methods of making and using the same.

19 Claims, 3 Drawing Sheets

BONE MARROW STEM CELL COMPOSITIONS, METHODS OF MAKING, AND USES THEREOF

CROSS-REFERENCE TO RELATED APPLICATIONS

This application is a continuation-in-part of currently pending U.S. Utility application Ser. No. 15/525,418, which is the 35 U.S.C. § 371 national stage application of PCT Application No. PCT/US2016/056617, filed on Oct. 12, 2016, where the PCT also claims the benefit of and priority to U.S. Provisional Patent Application No. 62/240,318, filed on Oct. 12, 2015, entitled "SOLUBLE BONE MARROW PROTEIN COMPOSITIONS, METHODS OF MAKING, AND USES THEREOF," and U.S. Provisional Patent Application No. 62/240,348, filed on Oct. 12, 2015, entitled "SCAFFOLD MATERIALS CONTAINING SOLUBLE BONE MARROW PROTEIN COMPOSITIONS, METHODS OF MAKING, AND USES THEREOF," the contents of which are expressly not incorporated by reference.

BACKGROUND

Bone and tissue grafting are surgical procedures that replace missing bone or other tissues to repair bone and other joint or other tissue damage. Generally, bone has the ability to regenerate completely but typically need some sort of scaffold to do so. Current bone grafts can be natural (allograft or autologous) or synthetic compositions that have similar mechanical properties as bone (e.g. hydroxyapatite). Despite the regenerative nature of bone, conditions are not always ideal for healing of the bone graft. Indeed, despite the efficacy of modern internal fixation techniques, infection, poor vascularity, malnutrition, and substantial bone or soft tissue loss can impede effective osteogenesis. As such there exists a need for improved compositions and methods for increasing the healing efficacy of existing bone and tissue grafting techniques.

SUMMARY

Provided herein are methods of making a composition that can contain living stems cells derived from bone marrow, that can contain the steps of harvesting bone marrow from a donor to obtain harvested bone marrow, where the bone marrow contains bone marrow cells, selectively lysing or rinsing the bone marrow cells to remove undesired cells (e.g. red and white blood cells) but retaining viable stem cells (e.g. bone marrow mesenchymal stem cells), decontaminating the remaining viable stem cells, and cryopreserving the stem cells remaining. The method can further include the step of wherein an amount of the composition that can contain viable stem cells is implanted in or otherwise administered to a subject in need thereof.

Also provided herein are compositions and implants that can contain viable stem cells, where the compositions can be made by a method that can include the steps of harvesting bone marrow from a donor to obtain harvested bone marrow, where the bone marrow contains bone marrow cells, selectively lysing or rinsing the bone marrow cells to remove undesired cells (e.g. red and white blood cells) but retaining viable stem cells (e.g. bone marrow mesenchymal stem cells), decontaminating the remaining viable stem cells, and cryopreserving the stem cells. The viable stem cells can contain one or more bioactive factors, which can be a protein selected from the group of: epidermal growth factor, an insulin-like growth factor, a fibroblast growth factor, vascular endothelial growth factor, oteoprotegerin, and osteopontin. The bioactive factors can be present in the composition or implant at a concentration of about 0 pg/g to about 100 mg/g. The bioactive factor can be bone morphogenetic protein 2 and can be present at a concentration of at least 1 pg/g. The bioactive factor can be acidic fibroblast growth factor and can be present at a concentration of at least 1 pg/g. The bioactive factor can be basic fibroblast growth factor and can be present at a concentration of at least 1 pg/g. The bioactive factor can be vascular endothelial growth factor and can be present at a concentration of at least 1 pg/g.

Also provided herein are methods of treating a subject in need thereof that can include the step of implanting or administering a composition or an implant to the subject in need thereof, where the composition or implant can include viable stem cells, where the composition is made by a method that can include the steps of harvesting bone marrow from a donor to obtain harvested bone marrow, where the bone marrow contains bone marrow cells, selectively lysing or rinsing the bone marrow cells to remove undesired cells (e.g. red and white blood cells) but retaining viable stem cells (e.g. bone marrow mesenchymal stem cells), decontaminating the remaining viable stem cells, and cryopreserving the stem cells. The subject in need thereof can have a bone fracture. The subject in need thereof can need a bone fusion. The subject in need thereof can be in need of a spinal fusion.

Also provided herein are implants that can contain an amount of a bone scaffold and a composition that can contain viable stem cells derived from bone marrow, where the composition further can contain an acid at a concentration or amount that retains stem cell viability. The scaffold can be in the form of a block/structures, chips, or morsels. The viable stem cells can contain a bioactive factor, which can be present in the composition at a concentration of at least at least 1 pg/g. The bioactive factor can be present in the composition at a concentration of about 0 µg/g to about 100 mg/g. The bioactive factor can be selected from the following group of: an epidermal growth factor, an insulin-like growth factor, a fibroblast growth factor, vascular endothelial growth factor, osteoprotegerin, and osteopontin, and combinations thereof. The bioactive factor can be insulin like growth factor-1. The bioactive factor can be α-fibroblast growth factor and can be present at a concentration of at least 1 pg/g. The bioactive factor can be β-fibroblast growth factor. The β-fibroblast growth factor can be present at a concentration of at least 1 pg/g. The bioactive factor can be vascular endothelial growth factor. The vascular endothelial growth factor can be present at a concentration of at least 1 pg/g.

Also provided herein are methods that can contain the step of implanting in or administering to a subject in need thereof an implant that can contain an amount of a composition or implant that can contain viable stem cells derived from bone marrow, which can contain a bioactive factor. The composition or implant can further contain an acid at a concentration or amount that retains the viability of the stem cells. The subject in need thereof can be in need of a bone graft or a bone fusion.

Also provided herein are methods that can include the step of implanting or administering an implant that can contain an amount of a scaffold and a composition or implant that can contain viable stem cells derived from bone marrow. The composition or implant can further contain an acid present at an amount or concentration that retains the viability of the stem cells, where the subject in need thereof can have a bone fracture, diseased bone, joint fracture, a diseased joint, or a combination thereof.

Also provided herein are methods of fusing a portion of a spine, where the method can contain the step of implanting or administering an implant that can contain an amount of a scaffold and composition that can contain viable stem cells derived from bone marrow. The composition or implant can further contain an acid at an amount or concentration that retains viability of the stem cells.

Also provided herein are methods of grafting bone where the method can contain the step of implanting or administering an implant that can contain an amount of a scaffold and a composition that can contain an amount of viable stem cells that are derived from bone marrow. The composition can further contain an acid at an amount or concentration that can retain the viability of the stem cells.

BRIEF DESCRIPTION OF THE DRAWINGS

Further aspects of the present disclosure will be readily appreciated upon review of the detailed description of its various embodiments, described below, when taken in conjunction with the accompanying drawings.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited unless expressly stated otherwise. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of molecular biology, microbiology, nanotechnology, organic chemistry, biochemistry, botany and the like, which are within the skill of the art. Such techniques are explained fully in the literature.

Definitions

As used herein, "about," "approximately," and the like, when used in connection with a numerical variable, generally refers to the value of the variable and to all values of the variable that are within the experimental error (e.g., within the 95% confidence interval for the mean) or within ±10% of the indicated value, whichever is greater.

As used herein, "adipocyte" refers to a cell type also known as a lipocyte or fat cell. Adipocytes are the cells that primarily compose adipose tissue, specialized in storing energy as fat.

As used herein, "additive effect" refers to an effect arising between two or more molecules, compounds, substances, factors, or compositions that is equal to or the same as the sum of their individual effects.

As used herein, "administering" refers to an administration that is oral, topical, intravenous, subcutaneous, transcutaneous, transdermal, intramuscular, intra-joint, parenteral, intra-arteriole, intradermal, intraventricular, intracranial, intraperitoneal, intralesional, intranasal, rectal, vaginal, by inhalation or via an implanted reservoir. The term "parenteral" includes subcutaneous, intravenous, intramuscular, intra-articular, intra-synovial, intrasternal, intrathecal, intrahepatic, intralesional, and intracranial injections or infusion techniques.

As used herein, "allogeneic" refers to involving, derived from, or being individuals of the same species that are sufficiently genetically different so as to interact with one another antigenicaly.

As used herein, "allograft" refers to a graft that is derived from one member of a species and grafted in a genetically dissimilar member of the same species.

As used herein, "autograft" refers to a graft that is derived from a subject and grafted into the same subject from which the graft was derived.

As used herein, "autologous" refers to being derived from the same subject that is the recipient.

As used herein, "bioactive" refers to the ability or characteristic of a material, compound, molecule, or other particle that interacts with or causes an effect on any cell, tissue and/or other biological pathway in a subject.

As used herein, "bioactive factor" refers to a compound, molecule, or other particle that interacts with or causes an effect on any cell, tissue, and/or other biological pathway in a subject.

As used herein, "biocompatible" or "biocompatibility" refers to the ability of a material to be used by a patient without eliciting an adverse or otherwise inappropriate host response in the patient to the material or a derivative thereof, such as a metabolite, as compared to the host response in a normal or control patient.

As used herein, "cell," "cell line," and "cell culture" include progeny. It is also understood that all progeny may not be precisely identical in DNA content, due to deliberate or inadvertent mutations. Variant progeny that have the same function or biological property, as screened for in the originally transformed cell, are included.

As used herein, "complete extracellular matrix" refers to extracellular matrix that has all components (proteins, peptides, proteoglycans, and the like) present and may or may not include other cells that are embedded in the extra cellular matrix.

As used herein, "concentrated" used in reference to an amount of a molecule, compound, or composition, including, but not limited to, a chemical compound, polynucleotide, peptide, polypeptide, protein, antibody, or fragments thereof, that indicates that the sample is distinguishable from its naturally occurring counterpart in that the concentration or number of molecules per volume is greater than that of its naturally occurring counterpart.

As used herein, "control" is an alternative subject or sample used in an experiment for comparison purposes and included to minimize or distinguish the effect of variables other than an independent variable.

As used herein, "culturing" refers to maintaining cells under conditions in which they can proliferate and avoid senescence as a group of cells. "Culturing" can also include conditions in which the cells also or alternatively differentiate.

As used herein, "decellularized extracellular matrix" refers to complete extracellular matrix that has been processed to remove any cells embedded within the extracellular matrix.

As used herein, "diluted" used in reference to an amount of a molecule, compound, or composition including but not limited to, a chemical compound, polynucleotide, peptide, polypeptide, protein, antibody, or fragments thereof, that indicates that the sample is distinguishable from its naturally occurring counterpart in that the concentration or number of molecules per volume is less than that of its naturally occurring counterpart.

As used herein, "donor" refers to a subject from which cells or tissues are derived.

As used herein, "effective amount" can refer to an amount sufficient to effect beneficial or desired results. An effective amount can be administered in one or more administrations, applications, or dosages.

As used herein, "endogenous" refers to a compound, substance, or molecule originating from within a subject or donor, including their cells or tissues.

As used herein, "extra cellular matrix" refers to the non-cellular component surrounding cells that provides support functions to the cell including structural, biochemical, and biophysical support, including but not limited to, providing nutrients, scaffolding for structural support, and sending or responding to biological cues for cellular processes such as growth, differentiation, and homeostasis.

As used herein, "extracellular matrix component" refers to a particular component. By way of a non-limiting example, an extracellular matrix comportment can be a specific class of comments (e.g. proteoglycans) or individual component (e.g. collagen I) that is separated or isolated from the other extracellular components. These components can be made synthetically.

As used herein, "exogenous" refers to a compound, substance, or molecule coming from outside a subject or donor, including their cells and tissues.

As used herein, "filler" refers to a substance used to fill a cavity or depression. The filler can fill the depression such that it is level with the surrounding area or that the cavity is filled, such that the depth of the depression or volume of the cavity is decreased, or such that the area that was the depression is now raised relative to the areas immediately surrounding the depression.

As used herein "hydrogel" refers to a network of hydrophilic polymer chains that are dispersed in water. "Hydrogel" also includes a network of hydrophilic polymer chains dispersed in water that are found as a colloidal gel.

As use herein, "immunogenic" or "immunogenicity" refers to the ability of a substance, compound, molecule, and the like (referred to as an "antigen") to provoke an immune response in a subject.

As used herein, "implant" or "graft," as used interchangeably herein, refers to cells, tissues, or other compounds, including metals and plastics, that are inserted into the body of a subject.

As used herein, "isolated" means separated from constituents, cellular and otherwise, with which the polynucleotide, peptide, polypeptide, protein, antibody, or fragments thereof, are normally associated in nature. A non-naturally occurring polynucleotide, peptide, polypeptide, protein, antibody, or fragments thereof, does not require "isolation" to distinguish it from its naturally occurring counterpart.

As used herein, "negative control" refers to a "control" that is designed to produce no effect or result, provided that all reagents are functioning properly and that the experiment is properly conducted. Other terms that are interchangeable with "negative control" include "sham," "placebo," and "mock."

As used herein, "physiological solution" refers to a solution that is about isotonic with tissue fluids, blood, or cells.

As used herein, "positive control" refers to a "control" that is designed to produce the desired result, provided that all reagents are functioning properly and that the experiment is properly conducted.

As used herein, "preventative" refers to hindering or stopping a disease or condition before it occurs or while the disease or condition is still in the sub-clinical phase.

As used herein "scaffold" can refer to bone or processed bone material.

As used interchangeably herein, "subject," "individual," or "patient," refers to a vertebrate, preferably a mammal, more preferably a human. Mammals include, but are not limited to, murines, simians, humans, farm animals, sport animals, and pets. The term "pet" includes a dog, cat, guinea pig, mouse, rat, rabbit, ferret, and the like. The term farm animal includes a horse, sheep, goat, chicken, pig, cow, donkey, llama, alpaca, turkey, and the like.

As used herein, "therapeutic" refers to treating or curing a disease or condition.

As used herein "self-assembling peptides" refer to peptides which undergo spontaneous assembly into ordered nanostructures. "Self-assembling peptides" include di-peptides, lego peptides, surfactant peptides, molecular paint or carpet peptides, and cyclic peptides.

As used herein, "specific binding" refers to binding which occurs between such paired species as enzyme/substrate, receptor/agonist, antibody/antigen, and lectin/carbohydrate which may be mediated by covalent or non-covalent interactions or a combination of covalent and non-covalent interactions. When the interaction of the two species produces a non-covalently bound complex, the binding which occurs is typically electrostatic, hydrogen-bonding, or the result of lipophilic interactions. Accordingly, "specific binding" occurs between a paired species where there is interaction between the two which produces a bound complex having the characteristics of an antibody/antigen or enzyme/substrate interaction. In particular, the specific binding is characterized by the binding of one member of a pair to a particular species and to no other species within the family of compounds to which the corresponding member of the binding member belongs. Thus, for example, an antibody preferably binds to a single epitope and to no other epitope within the family of proteins.

As used herein, "syngeneic" refers to subjects or donors that are genetically similar enough so as to be immunologically compatible to allow for transplantation, grafting, or implantation.

As used herein, "synergistic effect," "synergism," or "synergy" refers to an effect arising between two or more molecules, compounds, substances, factors, or compositions that is greater than or different from the sum of their individual effects.

As used herein "xenograft" or "xenogeneic" refers to a substance or graft that is derived from one member of a species and grafted or used in a member of a different species.

Discussion

Bone grafting is a common procedure performed for a variety of orthopedic and dental reasons. Many materials have been developed that can be used for bone graft procedures. Such materials include, but are not limited to, autograft, allograft, and synthetic bone graft materials. While these materials have enjoyed a certain amount of clinical success, donor morbidity when using autograft materials, adverse recipient immune response when using allograft materials, and limited bone remodeling and low osteoconductivity that can be observed when using synthetic materials. Attempts to improve the clinical performance of all types of materials have employed the use of recombinant or synthetic bioactive factors that are involved in the bone-remodeling process. While there have been attempts to obtain bioactive factors directly from various tissue sources, all have relied upon harsh chemicals or other conditions to isolate the bioactive factors, which does not retain viable cells and can lead to low yields of viable bioactive factors such and reduce clinical performance of the bioactive factors obtained. Further, the variability in the amount and type of cells or bioactive factors obtained directly from tissue sources due to the methods used to obtain the bioactive factors severely limits this approach for any practical clinical purpose.

With the aforementioned shortcomings in mind, described herein are compositions and implants that can include a composition that can contain viable stem cells derived from bone marrow provided herein. The compositions provided herein can, in some embodiments, overcome one or more of the shortcomings of existing implant materials. Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

Bone Marrow Stem Cell Compositions and Implants

Bone Marrow Stem Cell Compositions

Bone marrow is the soft, spongey, gelatinous tissue found in the hollow spaces in the interior of bones. Bone marrow contains stem cells that are supported by a fibrous tissue called the stroma. There are two main types of stem cells in bone marrow: (1) hematopoietic stem cells and (2) bone marrow mesenchymal stem cells (bmMSCs). bmMSCs can differentiate into a variety of cells types including without limitation, fibroblasts, chondrocytes, osteocytes, myotubes, stromal cells, adipocytes, astrocytes, and dermal cells. In addition to bmMSCs, bone marrow stroma contains other types of cells including fibroblasts (reticular connective tissue) macrophages, adipocytes, osteoblasts, osteoclasts, red blood cells, white blood cells, leukocytes, granulocytes, platelets, and endothelial cells.

The bone marrow stem cell compositions and implants described and provided herein can contain viable bone marrow mesenchymal stem cells, fibroblasts, chondrocytes, osteocytes, red blood cells, white blood cells, leukocytes, granulocytes, platelets, and/or osteoclasts. In some embodiments, the bone marrow stem cell compositions and implants selectively contain bone marrow stem cells (e.g. bone marrow mesenchymal stem cells) and not other types of cells (e.g. immunogenic cells, white blood cells, red blood cells, platelets, leukocytes, and/or granuloctes). In some aspects, the viable bone marrow stem cells can contain bioactive factors, which can be proteins. The proteins can be intracellular proteins or membrane associated proteins. Such proteins include, transforming growth factors (TGF-β1, TGF-β2), epidermal growth factor (EGF), hepatocyte growth factor (HGF), insulin-like growth factors (IGFs) (e.g. IGF-1), fibroblast growth factors (FGFs) (e.g. aFGF (acidic fibroblast growth factor) and bFGF (basic fibroblast growth factor)), vascular endothelial growth factor (VEGF), platelet derived growth factor-BB (PDGF-BB), osteoprotegerin (OPG), and osteopontin (OPN).

The bone marrow stem cell compositions and implants can contain viable bone marrow stem cells that have been cryopreserved. In some embodiments, the s bone marrow stem cell compositions and implants can be liquid or flowable solution. In some embodiments, the bone marrow stem cell compositions and implants can be frozen in such a way that the viability of at least some of the bone marrow stem cells is retained. Suitable cryopreservation techniques to retain the viability of bone marrow stem cells will be appreciated by one of ordinary skill in the art. In some embodiments, bone marrow stem cell compositions and implants can be frozen to less than about 0° C. such as −10, −20, and −80° C. or more. The bone marrow stem cell compositions and implants do not inherently contain recombinant proteins. The bone marrow stem cell compositions and implants as described herein can increase the efficiency of implant and/or graft integration and/or healing over that of the bone marrow stem cells if present in the context of complete bone marrow or other complete bodily fluid or tissue.

Additionally, the bone marrow stem cell compositions and implants described herein can lack or contain a reduced amount of the immunogenic proteins, cells, and other components that are present in complete bone marrow and/or other complete bodily fluid or tissue. The bone marrow stem cell compositions and implants provided herein, in some embodiments, do not include a recombinant or synthetic protein or other bioactive factor. In other words, in some embodiments the bone marrow stem cell compositions and implants can be non-recombinant bone marrow stem cell compositions and implants. In other embodiments, the bone marrow stem cell compositions and implants can contain one or more recombinant factors.

The bone marrow stem cells contained in the bone marrow stem cell composition or implants can contain a bioactive factor. Any particular bioactive factor in the bone marrow stem cells can be present in the bone marrow stem cell composition or implant at a concentration of 0 µg/g to about 100 mg/g of isolated protein in the final product (e.g. composition or implant), cryopreserved, or otherwise provided. The bone marrow stem cell compositions and implants can include at least about 1 pg/g aFGF, about 1 pg/g to about 100 µg/g aFGF, about 1 ng/g to about 100 ng/g aFGF, or about 20 to about 40 ng/g aFGF. The bone marrow stem cell compositions and implants can include at least about 1 pg/g bFGF, about 1 pg/g to about 100 µg/g bFGF, about 1 ng/g to about 100 ng/g bFGF, or about 20 ng/g to about 40 ng/g bFGF. The concentration of VEGF in the bone marrow stem cell compositions and implants can be at least about 1 pg/g, or about 1 pg/g to about 100 µg/g VEGF, about 1 ng/g to about 150 ng/g VEGF, or about 60 ng/g to about 90 ng/g VEGF. The bone marrow stem cell compositions and implants can include at least 1 pg/g PDGF, or about 1 pg/g PDGF to about 100 µg/g PDGF, about 500 pg/g to about 500 ng/g PDGF, about 900 pg/g to about 100 ng/g PDGF, or to about 950 pg/g to about 50 ng/g PDGF. The bone marrow stem cell compositions and implants can include at least 1 pg/g OPN, or about 1 pg/g OPN to about 100 µg/g OPN, about 500 pg/g OPN to about 500 ng/g OPN, about 900 pg/g to about 100 ng/g OPN, or to about 950 pg/g to about 50 ng/g OPN.

Additionally, the bone marrow stem cell compositions and implants can also contain an amount of a suitable acid or water at an amount or concentration that can retain the viability of the bone marrow stem cells present in the composition or implant. In some embodiments, the acid is a residual or other amount of the acid that can be used to selectively lyse the bone marrow cells to retain viable bone marrow stem cells (e.g. bone marrow mesenchymal stem cells) but lyse other cell types (e.g. red and white blood cells). In some embodiments, the acid can be acetic acid. In other embodiments, water can be used to selectively lyse the cells.

In some embodiments, the bone marrow stem cell compositions and implants composition can include a stabilizer composition or stabilizer compounds. Suitable stabilization compositions can include, but are not limited to glycerol, glucose, sucrose, amino acids, preservatives, antibiotics, antivirals, antifungals, pH stabilizers, osmostablizers, anti-inflammants, anti-neoplastics, chemotherapeutics, immuno-modulators, chemoattractants, growth factors, anticoagulants, nutrients, or combinations thereof. The stabilization solution can increase shelf life of the bone marrow stem cell compositions and implants and maintain the viability of the bone marrow stem cells present in the bone marrow stem cell compositions and implants prior to use.

In some embodiments, a bone marrow stem cell compositions and implants composition can be reconstituted. This can result in a dilution of the bone marrow stem cells within the bone marrow stem cell compositions and implants. In some embodiments, the bone marrow stem cell compositions and implants can be concentrated using a suitable concentration method such that the number of viable cells per cc or mg of composition or implant is increased in comparison to the starting material. The bone marrow stem cell compositions and implants can be diluted/concentrated from 0.1 to 100 fold, 0.1 to 50 fold, 0.1 to 20 fold, or 0.1 to 5 fold. Dilution or concentration can occur before or during use.

Implants Including a Bone Marrow Stem Cell Composition

Provided herein are bone marrow stem cell implants that can contain a grafting scaffold materials (also referred to herein as "scaffolds") that can include a bone marrow stem cell composition provided elsewhere herein that can have one or more viable stem cells of the composition bound adsorbed, absorbed, or otherwise attached to or associated with a scaffold material. The scaffolds can be bone material.

The bone marrow stem cell compositions can be any bone marrow stem cell composition provided herein. The bone marrow stem cell compositions including or not including the scaffold material can be cryopreserved. The bone marrow stem cell compositions and implants, proteins and/or other bioactive factor(s) can become diluted when contacted with bodily fluids, for example, when the bone material containing the bone marrow stem cell composition are implanted in or otherwise administered to a subject in need thereof. As described elsewhere herein, the bone marrow stem cell compositions can contain an amount of an acid or water in an amount or concentration that can retain the viability of the bone marrow stem cells contained in the composition or implant. The acid can be acetic acid. The acid can be a residual amount left over from the method of producing the bone marrow stem cell composition.

Scaffold Materials

The scaffold material can be a bone material, such as allograft, autograft, or xenograft bone. The bone material can be wholly or partially demineralized. The scaffold material can be sterilized.

Methods of Making the Bone Marrow Stem Cell Compositions and Implants

Described herein are methods for producing compositions containing viable bone marrow stem cells. In some embodiments, the viable bone marrow stem cells can attach to or otherwise associate with a scaffold prior to delivery to or use in a subject. The soluble protein compositions prepared by the methods described herein can have a greater amount and/or concentration of bone marrow stem cells and/or additional bioactive factor(s) contained within the viable stem cells, and/or less immunogenicity than other osteoinductive/osteostimulatory compositions, implants, or devices incorporating complete bone marrow and/or other complete bodily fluids or tissues. The bone marrow stem cell compositions and implants can contain bioactive proteins such as acidic-FGF, basic-FGF, IGF, BMP-7, HGF, VEGF, PDGF-BB, OPG, and OPN.

Figure 1:
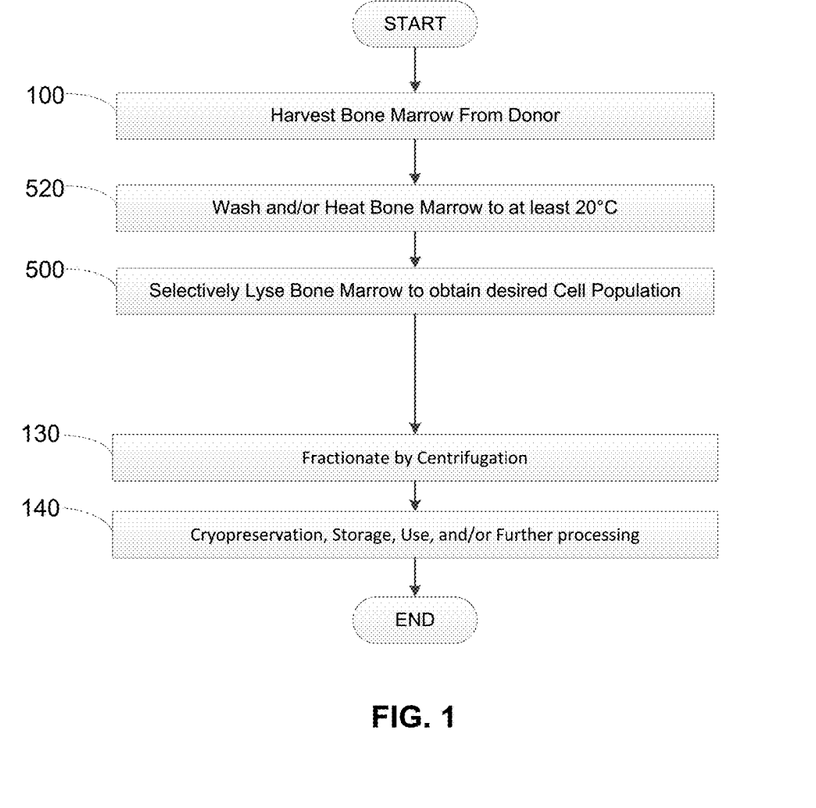
FIG. 1 shows an embodiment of a method of making a bone marrow stem cell composition or implant.

Attention is first directed to FIG. 1, which shows an embodiment of a method of producing a soluble protein composition from bone marrow. The bone marrow can be harvested from a cadaver or from a living subject. The method can begin by harvesting bone marrow from a donor 100. The donor can be a cadaver or can be a living subject. The bone marrow can be autologous, allogeneic or xenogenic. The bone marrow can be harvested in any way generally known in the art. The bone marrow can be obtained from cancellous, corticocancellous, and/or cortical bone. The harvest of the bone marrow may also include bone prior to washing. After the bone marrow has been harvested, the bone marrow can be washed 520 in a solution. The wash solution may contain water, saline, antibiotic, antiseptic, antifungal, or crystalloid solution.

In some embodiments, the wash solution is only water. Washing can take place at any temperature. In some embodiments, washing takes place at least at 20° C. In some embodiments, washing takes place at about 20° C. to about 37° C. In further embodiments, washing takes place at about 20° C. to about 40° C. In some embodiments, the washing takes place at 37° C. Heating the bone marrow during washing can facilitate the reduction in viscosity or removal of undesired fat (adipocytes) from other types of bone marrow cells. The washing/heating step can be performed under physical agitation in a shaker incubator. In some embodiments, shaking ca be conducted at about 10-300 rpm for up to about 24 hours. In some embodiments, shaking can be conducted for about 20, 40, 60, 120, 240, 260, 5, 6, 7, 8, 9, 10, 11, 12, 13, 14, 15, 16, 17, 18, 19, 20, 21, 22, 23 or 24 hours. When physical agitation is used, the conditions of the physical agitation are such that the viability of at least some of the bone marrow stem cells present in the bone marrow cells is retained.

During washing and/or heating 520, some of the bone marrow derived cells can be lysed. Under some conditions, substantially all of the bone marrow derived cells remain intact and viable after washing and/or heating 520. After heating and/or washing, the bone marrow cells can be selectively lysed 500. In some embodiments, the bone marrow derived cells can be selectively lysed using a selective lysing solution containing water, salt, or an acid configured to osmotically selective lyse some cells but not others that are resistant to the lysis conditions. In some embodiments the cells that are resistant to the selective lysing conditions are bone marrow stem cells (e.g. bone marrow mesenchymal stem cells). In some embodiments, the selective lysing solution is just water. In some embodiments, the washing solution and the selective lysing solution can be the same solution. In some embodiments, the selective lysing solution is acetic acid. In some embodiments, the selective lysis solution contains 0.5% v/v or less acetic acid. In some embodiments the lysing solution that contains the bone marrow and/or marrow-rich bone is mixed with preheated water. In some embodiments, the bone marrow or marrow-rich bone is selectively lysed 500 for about 60 minutes. In other embodiments, the bone marrow or marrow-rich bone is incubated in the selective lysing solution with shaking.

After selective lysing 500, the lysate that can contain viable cells can be optionally fractionated via centrifugation 130 to separate out particles present in the lysate based on their size or density. Such centrifugation techniques that can be employed include, but are not limited to, differential centrifugation, rate-zonal centrifugation, and isopycnic centrifugation. In embodiments where centrifugation is used to separate particles in the lysate based on density, a suitable density gradient medium can be used. Suitable density gradient mediums include, but are not limited to, sucrose, glycerol, sorbitol, Ficoll® medium, polysucrose, dextrans, CsCl, Cs$_2$SO$_4$, KBr, Diatrizoate, Nycodenz® medium, Histodenz™ medium, iodixanol, Histopaque® mediums, ACCUSPIN® medium, and Percoll® medium. One of ordinary skill in the art will appreciate that the type of medium used is dependent on the type of particle(s) that is desired to be separated out. One or more rounds of centrifugation can be applied to the lysate to further separate out different particles in the lysate. In some embodiments, the desired fraction contains viable bone marrow stem cells, such as bone marrow mesenchymal stem cells. In some embodiments, the lysate is centrifuged at about 100 to about 1,000, 2,000, 3,000, 4,000, 5,000, 6,000, 7,000, 8,000, 9,000, 10,000, to about 20000 rpm for about 1 to about 600 minutes. In some embodiments, the lysate is centrifuged at about 1 to about 4000×g. The lysate, in some aspects, can be centrifuged for about 10 minutes. In some aspects, the lysate can be centrifuged at room temperature or at about 4° C.

Figure 2:
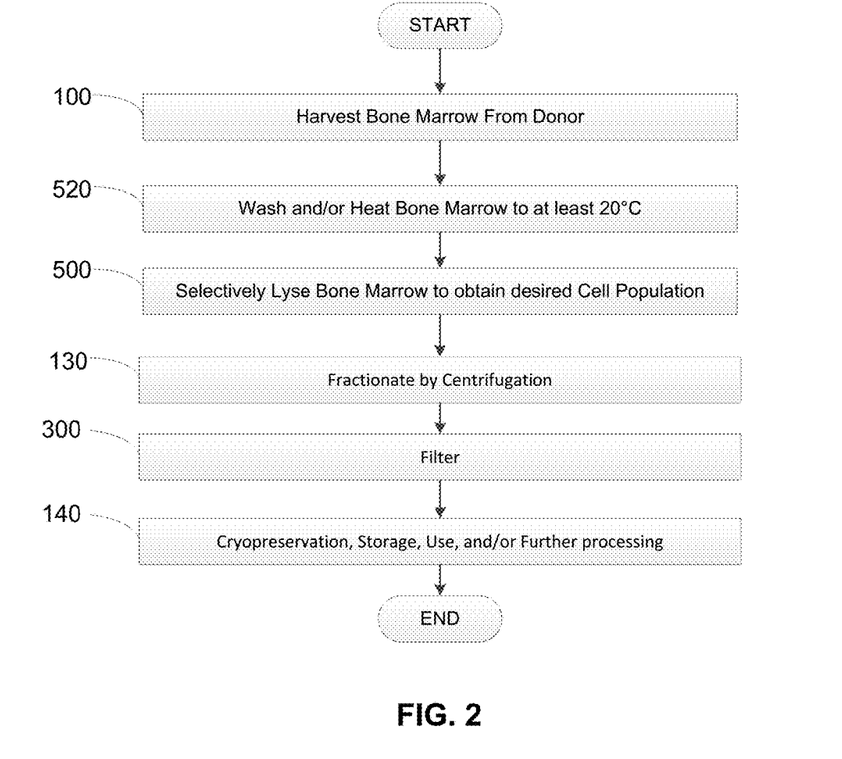
FIG. 2 shows an embodiment of a method of making a bone marrow stem cell composition or implant.

After the optional fractionation 130, the desired fraction that can contain viable bone marrow stem cells can be removed from the centrifuged lysate. The bone marrow stem cell containing fraction can then be optionally cryopreserved, otherwise stored, further processed, or used 140 using a suitable technique. With the general process described, attention is directed to FIGS. 2-3, As shown in FIG. 6, the method where the harvested bone marrow can be selectively lysed 500 prior during or prior to lysing (FIG. 5) can optionally include the step of filtering 300 the obtained fraction that contains the viable bone marrow stem cells after centrifugation 130. As shown in FIG. 2, after fractionation by centrifugation 130 the fraction containing the viable bone marrow stem cells can be further filtered using a suitable filtration technique to remove additional undesired components that can remain in the fraction. Suitable filtration techniques can include, but are not limited to, size exclusion techniques and/or affinity purification techniques, immunoseparation techniques, and charged based separation techniques. In some embodiments, additional undesired components can include, but are not limited to, nucleic acids such as DNA and RNA, and other compounds such as hemoglobin, globin proteins, cell fragments, cell membrane molecules and other molecules that can stimulate an immune response in a subject. In some embodiments, the filter can be low protein binding. In some embodiments, the filter can be high DNA binding.

In some embodiments, the filter can preferentially bind or retain one cell type over another or other components in the retained fraction. Suitable materials for some filters used in the filtration step 300, include, but are not limited to, Teflon® membranes, nylon membranes, PVDF (polyvinylidene) membranes, polypropylene, cellulose acetate, PES (polyethersulfone), regenerated cellulose, glass fiber, and PTFE (polytetrafluorethylene. In some embodiments, the filter can have a size cutoff of about 0.1 to about 3.0 μM. In some embodiments multiple filters can be used, such as in a serial filtration system. In such a system, multiple types of filters can be used. The system can include at least two filters that differ in material and size cut offs. In some embodiments, polypropylene filters (e.g. size cut offs of 30 μm and 10 μm can be used), a glass fiber filter with a size cutoff of about 2.7 μm can be used, and/or a series of cellulose acetate filters (8 μm, 5 μm, 3 μm, 1.2 μm, 0.8 μm, 0.45 μm and final one of 0.2 μm) can be used to filter. The filters can be configured as syringe filters, disc filters, vacuum filter systems, bottle top vacuum filters, tube top vacuum filters, or centrifuge tube filters.

Figure 3:
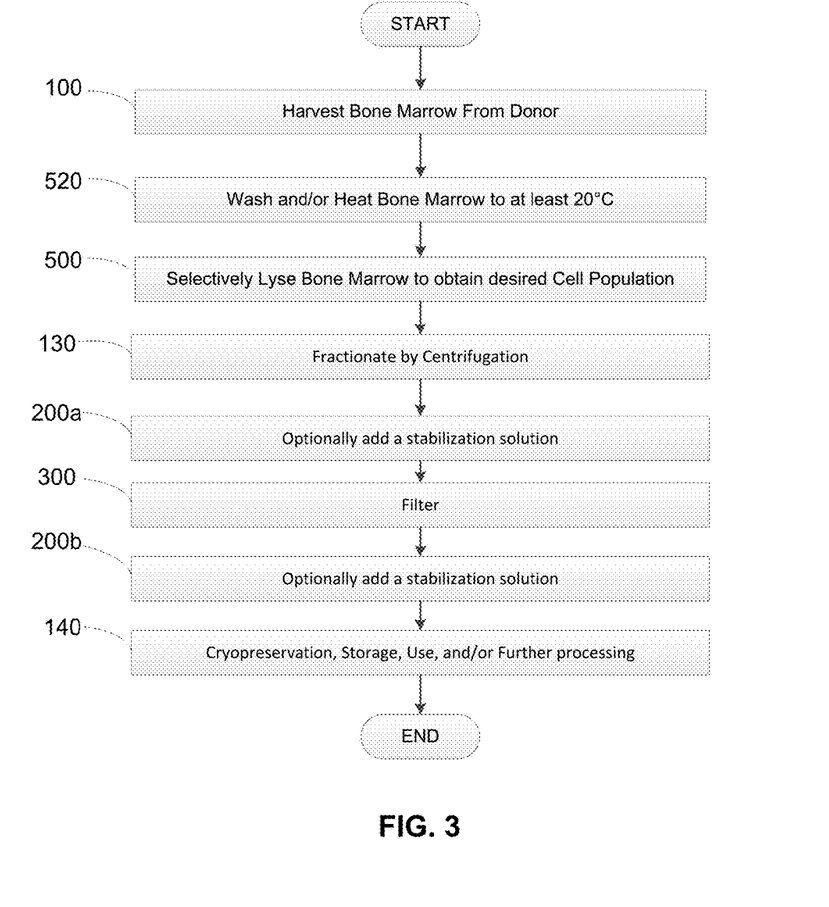
FIG. 3 shows an embodiment of a method of making a bone marrow stem cell composition or implant.

After filtering 300, the filtrate that contains the viable bone marrow stem cells can be cyropreserved, stored, further processed, and/or used as previously described. As shown in FIG. 3, the methods (FIG. 1 and FIG. 2) where the harvested bone marrow can be selectively lysed 500 prior to or during lysing can also include the optional step of adding a stabilization solution 200*a,b* after centrifugation 130 and/or filtration 300.

It will be appreciated that other steps can be included in any of the methods described herein. In some embodiments, the method can include a pH altering step where an acid or a base or an acidic or basic solution can be added to product of any step in any method to result in a product that is acidic (pH less than 7), basic (pH greater than 7), or neutral (pH of 7). In some embodiments, after lysing, the lysate or product from any other subsequent step can be made more acidic, neutral, or basic as desired. In embodiments, the bone marrow stem cell compositions and implants containing bone marrow stem cells (e.g. bone marrow mesenchymal stem cells) contains an acid that was introduced in the lysing step (e.g. 500). In other embodiments, the stabilization solution can contain an acid or base that can result in an acidic, basic, or neutral solution.

In some embodiments, the method can include a concentration step, where the product of any step in any embodiment of the method can be concentrated by a suitable technique. In some embodiments, the method can include a dilution step, where the product of any step in any embodiment of the method can be diluted by a suitable technique. Suitable concentration techniques include but are not limited to, dehydration techniques (described elsewhere herein) and centrifugation based techniques. Other concentration techniques will be appreciated by those of skill in the art.

Methods of Making Implants Containing a Bone Marrow Stem Cell Compositions

Methods of making the scaffold material, including bone material, are generally known in the art. Methods of making the bone marrow stem cell compositions are described herein. In some embodiments, the scaffold material can be introduced during the production of making a bone marrow stem cell composition where the scaffold material is mixed in at a step, such as the initial washing and/or selective lysing step with the initial starting bone marrow material. In other embodiments, the bone marrow stem cell composition can be mixed with the scaffold material after generating the bone marrow stem cell composition or during administration of the stem cell composition to a subject.

Methods of Using the Bone Marrow Stem Cell Compositions and Implants

The bone marrow stem cell compositions and implants described herein that can contain viable bone marrow stem cells. In some embodiments, the bone marrow stem cell compositions and implants described herein that can contain viable bone marrow stem cells can contain an acid at an amount or composition that retains cell viability of the stem cells in the composition or implant. The bone marrow stem cell compositions and implants described herein that can contain viable bone marrow stem cells can be implanted into or otherwise administered to a subject in need thereof. In some embodiments, an effective amount of the bone marrow stem cell compositions and implants described herein can be implanted or otherwise administered to a subject in need thereof. When implanted or administered, the bone marrow stem cell compositions and implants described herein can be diluted by the bodily fluids of the subject.

The bone marrow stem cell compositions and implants described herein to a suitable scaffold described elsewhere herein or a device. The scaffold can be flowable or non-flowable.

The bone marrow stem cell compositions and implants described herein can be applied to a scaffold or implant which is already present in a subject or can be implanted into a subject in need thereof. In other embodiments, the bone marrow stem cell compositions and implants described herein can be applied directly into a scaffold already present in the subject in need thereof.

In some embodiments, the method can include the step of implanting or otherwise administering a bone marrow stem cell compositions and implants described herein to a subject in need thereof. In some embodiments, a method of treating a subject in need thereof can include the step of implanting or otherwise administering bone marrow stem cell compositions and implants described herein to the subject in need thereof.

In some embodiments, the subject in need thereof needs a bone graft or bone fusion. In some embodiments, the subject in need thereof has a bone and/or joint fracture or disease. In some embodiments, the subject in need thereof needs a spinal fusion. In some embodiments the compositions described herein can be used in patients with low bone density to prophylactically help reduce, delay, or prevent bone loss or fracture.

In some embodiments, a method of fusing a portion of the spine, where the method includes the step of implanting or administering bone marrow stem cell compositions and implants described herein described herein to a subject in need thereof. In some embodiments, a method of bone grafting, where the method includes the step of implanting or administering bone marrow stem cell compositions and implants described herein described herein to a subject in need thereof.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Example 1

Red bone marrow can be extracted or harvested from flat bones. After extraction, can selective lysis can be performed on the extracted bone marrow or a desired cell population therein. This can be achieved by exposing the bone marrow to a lysing agent that selectively lyses red blood cells and white blood cells from the bone marrow but does not lyse the stem cells. One method of selectively lysing cells is to subject the cells to osmotic lysis. Osmotic lysis can be performed using water or weak acetic acid (less than or equal to 0.5% v/v). The lysing agent may be heated prior to exposure to the bone marrow cells. An anticoagulant may be added to the lysing agent to decrease platelet activation. The implant can then be treated with antibiotics and/or antifungals to further decontaminate the implant. After antibiotic treatment, the implant may be combined with demineralized bone and placed into a cryoprotectant prior to freezing. Freezing may be done in a stepwise manner to more slowly freeze the stem cells and preserve cell viability and function.

Example 2

An enriched stem cell implant may be produced by marrow rich bone where the bone marrow cells are not extracted from the bone but rather be included with and/or attached to cancellous bone. A rinsing agent, such as saline, can be used to wash away unattached cells which eliminates the majority of red blood cells and white blood cells. The rinsing agent may be heated prior to exposure to the bone marrow cells. An anticoagulant may be added to the rinsing agent to decrease platelet activation. The implant may then be treated with antibiotics and/or antifungals to further decontaminate the implant. After antibiotic treatment, the implant may be combined with demineralized bone and placed into a cryoprotectant prior to freezing. Freezing may be done in a stepwise manner to more slowly freeze the stem cells and preserve cell viability and function.

Example 3

An enriched stem cell implant that can contain viable bone marrow stem cells can be produced by utilizing bone marrow rich bone where bone marrow cells are included with and/or attached to cancellous bone, such as granules, blocks, or structures. A lysing agent, such as water or 0.5% (v/v) acetic acid, can be used to wash away and lyse unattached cells which eliminates the majority of red blood cells and white blood cells. The lysing agent can also selectively lyse white blood cells attached to the bone such as granulocytes. The lysing agent can be heated prior to exposure to the bone marrow cells. An anticoagulant can be added to the lysing agent to decrease platelet activation. The implant can then be treated with antibiotics and/or antifungals to further decontaminate the implant. After antibiotic treatment, the implant can be combined with demineralized bone and placed into a cryoprotectant prior to freezing. Freezing can be done in a stepwise manner to more slowly freeze the stem cells and preserve cell viability and function.

Example 4

The implant containing bone marrow stem cells may be tested for sterility after production by determining bioburden or by methods of USP 71. The implant can be stored at temperatures around −80° C. or colder and shipped for implantation on dry ice or liquid nitrogen. After production of the implant, cell viability can be evaluated by soaking the implant in collagenase to release the attached stem cells and observed under a microscope with trypan blue staining. Stem cell function and osteogenic differentiation ability can also be determined by culturing the unattached stem cells in osteogenic medium. Prior to implantation, the implant can be thawed and rinsed to remove any remaining cryoprotectant.

We claim:

1. A method of making a bone marrow stem cell composition or implant containing viable stem cells, the method comprising:
    harvesting bone marrow from a cadaver donor to obtain harvested bone marrow;
    heating the harvested bone marrow to about 20° C. to about 40° C.;
    selectively lysing the harvested bone marrow to obtain bone marrow stem cells, wherein the step of selectively lysing is performed using water or a solution containing 0.5% or less v/v acetic acid, wherein the step of selective lysing occurs at about 20° C. to about 40° C., and wherein one or more of the bone marrow stem cells are viable.

2. The method of claim 1, wherein the method further comprises the step of washing the harvested bone marrow prior to selectively lysing the harvested bone marrow.

3. The method of claim 1, wherein the method further comprises the step of centrifuging after the step of selectively lysing the harvested bone marrow.

4. The method of claim 1, wherein the method further comprises the step of filtering after the step of selectively lysing the harvested bone marrow.

5. The method of claim 1, wherein the method further comprises the step of adding a stabilization solution after the step of selectively lyisng the harvested bone marrow.

6. The method of claim 1, further comprising the step of mixing the bone marrow stem cell composition or implant with a scaffold material after the step of selectively lysing the harvested bone marrow.

7. The method of claim 6, wherein the scaffold material is allograft bone.

8. The method of claim 1, further comprising the step of adding a scaffold material after the step of harvesting the bone marrow and before the step of lysing.

9. The method of claim 8, wherein the scaffold material is allograft bone.

10. The method of claim 6, wherein at least one of the bone marrow stem cells is attached to the scaffold material.

11. The method of claim 7, wherein at least one of the bone marrow stem cells is attached to the allograft bone.

12. The method of claim 8, wherein at least one of the bone marrow stem cells is attached to the scaffold material after the step of lysing.

13. The method of claim 9, wherein at least one of the bone marrow stem cells is attached to the allograft bone after the step of lysing.

14. The method of claim 1, further comprising delivering the bone marrow stem cell composition or implant to a subject.

15. The method of claim 6, further comprising delivering the bone marrow stem cell composition or implant to a subject.

16. The method of claim 7, further comprising delivering the bone marrow stem cell composition or implant to a subject.

17. The method of claim 8, further comprising delivering the bone marrow stem cell composition or implant to a subject.

18. The method of claim 9, further comprising delivering the bone marrow stem cell composition or implant to a subject.

19. The method of claim 1, wherein the step of heating, the step of lysing, or both the steps of heating and lysing are performed at about 37° C.

* * * * *